(12) United States Patent  
Souchay et al.

(10) Patent No.: US 7,697,661 B2  
(45) Date of Patent: Apr. 13, 2010

(54) METHOD FOR OBTAINING A TOMOSYNTHESIS IMAGE

(75) Inventors: Henri Souchay, Versailles (FR); Ibrahima Faye, Courbevoie (FR); Razvan Gabriel Iordache, Paris (FR)

(73) Assignee: General Electric Company, Schenectady, NY (US)

( * ) Notice: Subject to any disclaimer, the term of this patent is extended or adjusted under 35 U.S.C. 154(b) by 309 days.

(21) Appl. No.: 11/830,902

(22) Filed: Jul. 31, 2007

(65) Prior Publication Data

US 2008/0056441 A1    Mar. 6, 2008

(51) Int. Cl.  
*A61B 6/04* (2006.01)

(52) U.S. Cl. .......................... 378/37; 378/21
(58) Field of Classification Search ............. 378/4, 378/37, 21–22  
See application file for complete search history.

(56) References Cited

U.S. PATENT DOCUMENTS

| | | | | |
|---|---|---|---|---|
| 5,526,394 | A * | 6/1996 | Siczek et al. | 378/37 |
| 7,092,482 | B2 * | 8/2006 | Besson | 378/37 |
| 7,123,684 | B2 * | 10/2006 | Jing et al. | 378/37 |
| 7,319,734 | B2 * | 1/2008 | Besson et al. | 378/37 |
| 7,463,713 | B2 * | 12/2008 | Mertelmeier | 378/22 |
| 2001/0038681 | A1 * | 11/2001 | Stanton et al. | 378/55 |
| 2003/0076988 | A1 * | 4/2003 | Liang et al. | 382/131 |
| 2003/0081734 | A1 * | 5/2003 | Nicolas et al. | 378/205 |
| 2007/0242797 | A1 * | 10/2007 | Stewart et al. | 378/16 |

FOREIGN PATENT DOCUMENTS

WO    WO 2005009206    2/2005

OTHER PUBLICATIONS

Wu et al., Tomographic mammography using a limited number or low-dose cone-beam projection images, Med Phys, 30, Mar. 3, 2003, pp. 365-380.*  
Links et al., Wiener Filtering Improves Quantification of Regional Mycoardial Perfusion with Thallium-201 SPECT, The Journal of Nuclear Medicine, vol. 31, No. 7, Jul. 1990, pp. 1230-1236.*  
Lu et al., Noise Properties of Low-Dose CT Projections and Noise Treatment by Scale Transformations, IEEE, Mar. 2002, pp. 1662-1666.*

* cited by examiner

*Primary Examiner*—Chih-Cheng G Kao  
*Assistant Examiner*—Alexander H Taningco  
(74) *Attorney, Agent, or Firm*—Global Patent Operation; Jonathan E. Thomas

(57) ABSTRACT

In a method for the obtaining a tomosynthesis image for a more selective detection of radiology signs, a dose distribution strategy is proposed. The strategy is defined as a function of a substantially uniform depth-of-focus for a variety of sizes and classes of radiology signs. This strategy is coupled with a digital filtering aimed at ensuring optimum propagation of the signal-to-noise ratio beyond the frequency spectrum. This digital filtering is done by means of a class of adaptive filters required to control the propagation of the noise during the reconstruction. The filter to be applied to each projection of the X-ray tube (4) depends on the dose assigned to this projection.

11 Claims, 4 Drawing Sheets

METHOD FOR OBTAINING A TOMOSYNTHESIS IMAGE

FIELD OF THE INVENTION

An object of the invention is a method for obtaining a tomosynthesis image for a more selective detection of radiology signs. The present invention can be applied to special advantage but not exclusively in the field of medical imaging and more particularly the field of mammography. The present invention also relates to a medical image reviewing station comprising an image-processing method of this kind.

PRIOR ART

Mammography is now widely used for the early detection of lesions associated with breast cancer. The radiology signs to be detected in mammography machines may be either calcium accretions known as microcalcifications which constitute elements more opaque to X-rays than the surrounding tissues or tumors which are expressed in the mammography image by dense zones in which the X-rays are more strongly absorbed then the adjacent zones.

Radiography images are acquired by means of an X-ray mammography apparatus designed to take radiography pictures of patients' breasts. Structurally, and by virtue of its principle, a mammography device has a column that is vertical, can be oriented obliquely and is provided with a breast-support tray or platform on which a patient places her breast. The breast-support tray or platform is superimposed either on a radiosensitive film for the detection of a radiography image or an electronic detector. The image acquisition protocols include the need to compress the breast at the time of the radiography. To this end, the column has a hand-operated or motor-driven sliding pad or paddle capable of compressing the breast. The top of the column has an X-ray tube and instruments used to collimate the X-ray beam. The column therefore bears the following elements vertically, from the top downwards: the X-ray tube, the paddle, the breast-support tray and the detector However, a mammography machine of this kind produces only a 2D image of the patient's breast which does not provide sufficient information on the presence of a tumor or a calcification and often gives rise to falsely positive interpretations which are both stressful to the patient and entail excessive public health costs.

Furthermore, it happens that certain calcium deposits and certain cases of opacity are not identified. This phenomenon has several causes. In particular, since the mammography images are the result of projections, they represent superimposed structures that disturb the visibility of the structures of the breast, sometimes leading either to a falsely positive interpretation when a superimposition of these structures resembles an opacity or to a falsely negative interpretation when these structures obscure the visibility of a lesion.

To help resolve these problems of falsely positive or falsely negative interpretations, there are mammography machines in the prior art that produce a 3D image of the patient's breast. FIG. 1a provides a schematic view of the principle of acquisition of a 3D image of the patient's breast. With the apparatus of FIG. 1a, rather than acquire an image by continuous integration of the irradiation on an X-ray sensitive film, it is preferred to acquire a series of images corresponding to a set of exposures made with the X-ray tube 4 of the mammography machine, placed at different positions P'n to Pn along a path T. The patient's breast 2 and hence the detector 3 are irradiated during these consecutive exposures P'n to Pn.

By then applying image reconstruction algorithms of the type used in computerized tomography, there are known ways of rebuilding the image in a slice plane well as other images in planes adjacent to the slice plane. Thus, we can speak of synthesis tomography in which all the images are required in a single scan. Any plane parallel to the detector in the breast may be produced retrospectively from the series of acquired images. Thus, from the series of images acquired in projection, a set of image slices extended over the thickness of the compressed breast is produced. Each section 5a to 5n represents a virtual section parallel to the plane of the detector at a distance z.

FIG. 1b provides a schematic view of two virtual slices parallel to the plane of the detector of the image volume produced. As can be seen in FIG. 1b, regions 6 and 7 of clinical interest in the breast 2 are distributed on all the sections, relative to their slicing planes, while at the same time minimizing interference with the surrounding tissues.

However, this tomosynthesis mammography apparatus has limitations. For, in such tomosynthesis apparatuses, a digital volume reconstruction of typically 50 to 80 slices is made for an average breast. Consequently, the quantity of information to be managed is very great. Similarly, access to a piece of information of clinical interest takes much more time because this piece of information is sought sequentially in the image volume.

Another problem, which is more specific to mammography but could arise in other fields, is related to the need to be able to analyze microcalcifications which become clinically interesting between 100 µm and 500 µm. Consequently, the detection and characterization of the anomalies by which a cancer lesion can be suspected in mammography necessitate high spatial resolution. This problem of spatial resolution is critical in tomosynthesis mammography devices. These devices therefore cannot be used to obtain sufficient image quality for a fine analysis of the microcalcifications.

Furthermore, one expected impact of such acquisition geometries is that tiny objects such as microcalcifications could become less obvious or not be located. For, the out-of-plane zones 6 and 7 of clinical interest suffer from a fuzzy spot function induced firstly by the reconstruction algorithm and secondly by the volume reconstruction of the entire breast. This volume reconstruction of the entire breast cannot be done with sufficient resolution along the projection axis except by generating a huge volume of data. This has the consequence of greatly affecting the process of examining the tomography images.

Furthermore, the individual loss of microcalcifications is not the only expected impact since, for clusters of microcalcifications, there is an additional, simultaneous loss of visibility of microcalcifications in the clusters due to reduced depth-of-focus. This depth-of-focus represents the quantity which can be made to vary without seriously impairing the sharpness of the image, below or beyond the exact plane of focus.

In the prior art, there is an approach to the problems of the workflow and display depth-of-focus. This approach is disclosed by Tao Wu et al in an article in "Medical Physics" March 2003 Vol 30 365/380. The solution described by Tao Wu et al describes a strategy for the distribution of the totality of the X-ray intensities, commonly called a dose. This strategy implements a non-uniform distribution of the irradiation dose produced by the X-ray tube during the exposure of the breast. This distribution is done as a function of the position of the tube relative to the breast and the motion of the detector.

This approach disclosed in an article by Tao Wu et al is shown in FIG. 2. In FIG. 2, the positions of the tube are distributed angularly between two borderline positions Pn and P'n, in groups of orientations of the tube. The groups are situated on either side of a middle position P0 of the tube. For all the orientations of a group, an irradiation dose is the same.

For a borderline group G3 or G'3, for which the positions of the tube are as close as possible to a borderline position Pn or P'n, the accumulated irradiation dose is equal to 0.33 of the total irradiation dose. For a middle group G1, for which the positions of the tube are distributed on either side of the middle position, the accumulated irradiation dose is equal to the total irradiation dose. For an intermediate group G2 or G'2 placed between the middle group G1 and the borderline group G3 or G'3, the accumulated irradiation dose is equal to 0.5 of the total irradiation dose.

In this proposed approach, reconstructed slices are combined digitally and together to obtain increased depth-of-focus. However, this does not resolve the potential loss of microcalcifications which are due to out-of-plane regions of clinical interest and do not produce an additional volume of data to be combined with the slices. Furthermore, the workflow may be impaired when the combination of the slices is done at the same time as the display.

SUMMARY OF THE INVENTION

The invention is aimed precisely at overcoming the drawbacks of the techniques explained here above. To this end, the invention proposes a method for obtaining a tomosynthesis image by which it is possible to detect radiology signs with better selectivity.

To this end, the invention proposes projection image acquisition techniques associated with an image processing method used to facilitate the detection of radiology signs in the 3D image. With the acquisition technique and the image processing method, the radiology signs are easier to identify in the tomosynthesis method, thus enabling examination with greater efficiency.

The invention proposes a novel approach to mammography that advantageously exploits the techniques of digital processing of the radiology image to improve the readability of the information.

These image-processing methods can be used to cope with a substantial quantity of data in developing novel strategies capable of reducing the time taken to review clinical data and of simplifying access to information of clinical interest.

The acquisition techniques of the invention can be used to acquire tomosynthesis sequences with an improved strategy for the distribution of the X-ray dose. With the invention, it can be shown that any dose distribution strategy whatsoever that brings about a correction of the prior art strategy leads to improved detection of radiology signs.

The dose distribution strategy of the invention is defined as a function of a depth-of-focus that is substantially uniform for a variety of sizes and classes of radiology signs. This strategy is coupled with a digital filtering aimed at ensuring optimal propagation of the signal-to-noise ratio above the frequency spectrum. This digital filtering is done by means of a class of adaptive filters required to control propagation of the noise during the reconstruction. In the invention, the filter to be applied to each projection of the tube depends on the dose assigned to this projection.

The invention thus implements a method for obtaining a particular tomosynthesis image where the appropriate distribution of the acquisition geometries and/or of the acquisition dose and/or of the digital filtering provides a depth-of-focus that is appropriate to the different sizes and classes of radiology signs to be detected. The invention has also highlighted the fact that a dose distribution strategy peaking at an angle close to the optical axis of the reconstruction, i.e. the perpendicular to the slice planes, sharply improves the quality of the image to be displayed, with ratios of 3 to 1 between the middle position and a borderline position of the tube.

More specifically, an object of the invention is a method for obtaining a tomosynthesis image in which:
- a body is subjected, during an exposure, to an X-ray irradiation by means of an X-ray tube for which the main direction of the irradiation is oriented at a first angle of orientation relative to the body,
- a first projection image corresponding to this first orientation is recorded,
- these operations are reiterated for other orientations of the main direction of orientation and other projection images are recorded,
- the projection images are processed to produce a reconstructed image,
- an irradiation dose produced by the X-ray tube is made to vary during the exposure, as a function of the orientation of the main direction relative to the body, or of other factors linked to the orientation,
- the orientations are distributed angularly between two borderline orientations in groups of orientations, wherein one orientation or one group of orientations is favored relative to the multiplicity of orientations of the path, the accumulated irradiation dose of the favored orientation or of the favored group of orientations is greater then ⅝th of the total irradiation dose.

Advantageously again according to the invention:
- the groups are situated on either side of a middle orientation whose main direction is perpendicular to a support of the body,
- for a borderline group, whose orientations are closest to the borderline orientation, the accumulated irradiation dose is smaller than 1/9th of the total irradiation dose,
- for a middle group, whose orientations are distributed on either side of the middle orientation, the accumulated irradiation dose is greater then ⅝th of the total irradiation dose.
- for an intermediate group placed between the middle group and a borderline group, the number of orientations of the group is smaller than the number of orientations of a borderline group.

An object of the invention is also a method for obtaining a tomosynthesis image wherein:
- a body is subjected, during an exposure, to an X-ray irradiation by means of an X-ray tube for which the main direction of the irradiation is oriented at a first angle of orientation relative to the body,
- a first projection image corresponding to this first orientation is recorded,
- these operations are reiterated for other orientations of the main direction of orientation and other projection images are recorded,
- the projection images are processed to produce a reconstructed image,
- an irradiation dose produced by the X-ray tube is made to vary during the exposure, as a function of the main direction relative to the body,
- the orientations are distributed angularly between two borderline orientations situated on either side of a middle orientation, an irradiation dose for an exposure oriented close to a borderline orientation being smaller than an irradiation dose for an exposure oriented close to the middle orientation
wherein
the processing comprises a spatial filtering of the projection images,
the spatial filtering comprises a filtering core of a given size,
the size of the core being smaller for the projection images corresponding to orientations close to the middle orientation than it is for the projection images corresponding to the orientations close to the borderline orientation.

Advantageously again according to the invention, the assigned dose and the size of the core vary gradually and monotonically with the identification of the angle of orientation relative to the middle orientation.

Advantageously again according to the invention, the filters are Wiener filters and the values of the filters for the orientations close to the middle orientation are greater than the values of the filters for the orientations close to the borderline orientation.

Advantageously again according to the invention, an angular pitch which is the angle formed by two consecutive orientations increases towards the borderline orientation.

Advantageously again according to the invention, the orientations close to the middle orientation have an angular pitch equal to about 3 degrees and the orientations close to the borderline orientation have their angular pitch equal to about 7 degrees.

Advantageously again according to the invention, the middle orientation is oriented perpendicularly to a support of the body, this support being placed so as to be facing the X-ray tube.

Advantageously again according to the invention, the exposure is fixed or mobile.

Advantageously again according to the invention, the body is a breast.

Advantageously again according to the invention, the reconstructed image is cut into one or more slices relative to a slicing plane parallel that of the detector.

Advantageously again according to the invention, the irradiation dose produced by the tube is determined as a function of the thickness of the patient's breast.

The invention also relates to a device for the implementation of said method.

BRIEF DESCRIPTION OF THE DRAWINGS

The invention will be understood more clearly from the following description and the accompanying figures. These figures are given by way of an indication and in no way restrict the scope of the invention.

DETAILED DESCRIPTION OF EMBODIMENTS OF THE INVENTION

Figure 1A:
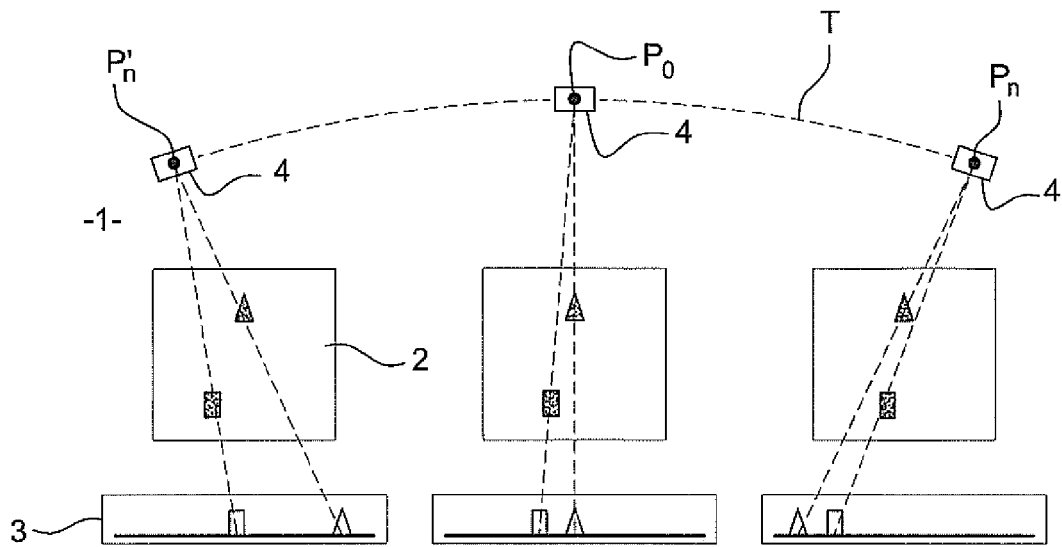
FIG. 1a, already described, is a schematic view showing the principle of acquisition of a tomosynthesis image.
Figure 1B:
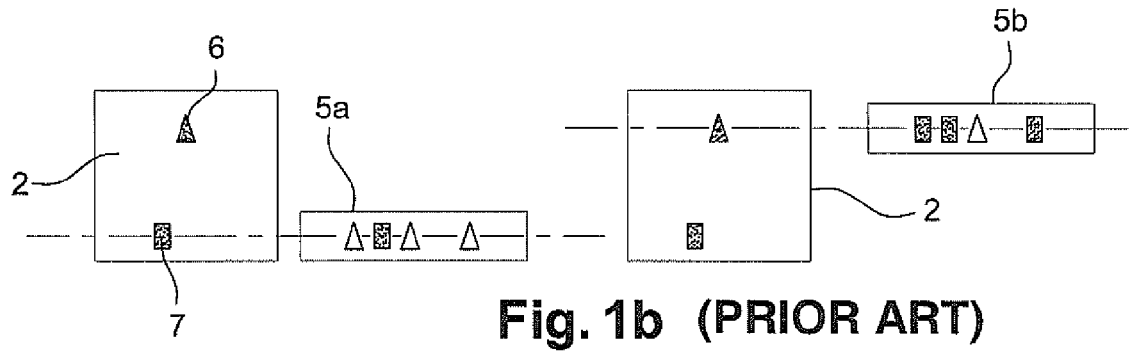
FIG. 1b, already described, is a schematic view of slices of the reconstructed digital volume of the breast.
Figure 2:
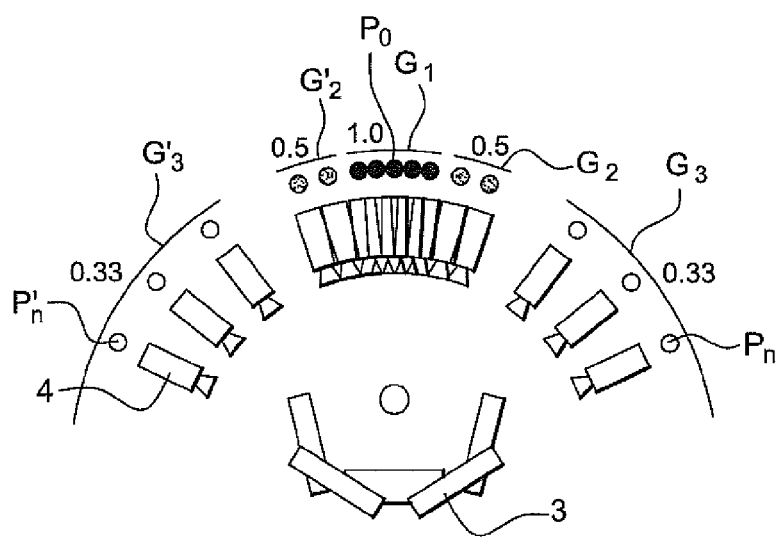
FIG. 2, already described, is a schematic view of a strategy of distribution of X-ray doses.
Figure 3:
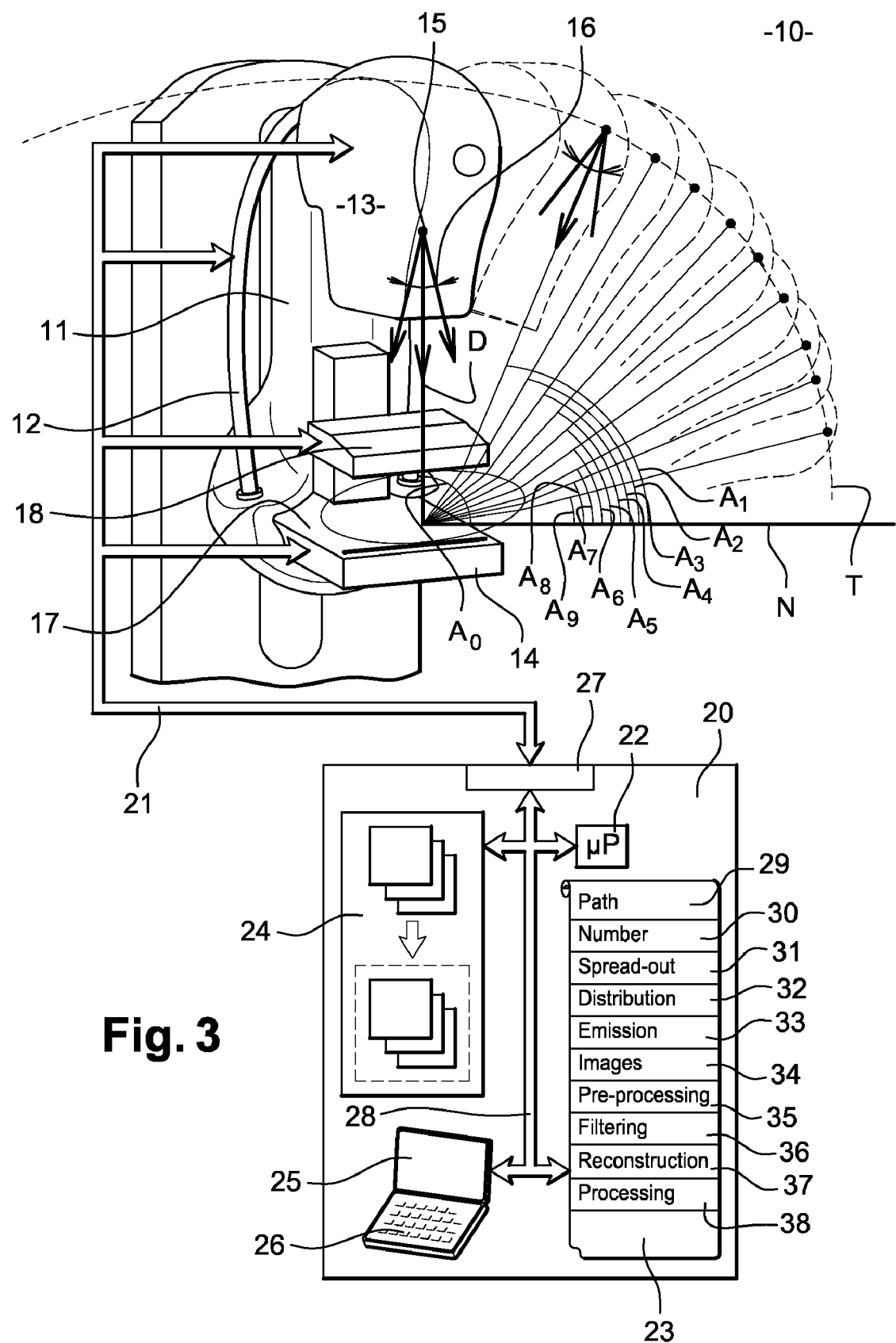
FIG. 3 is a schematic view of an X-ray device, especially a mammography machine, provided with the improved means of the invention.

FIG. 3 shows an X-ray device, especially a mammography machine, according to the invention. This X-ray device 10 has a vertical column 11. On this vertical column 11, there is a hinged arm 12 bearing an X-ray-emitting tube 13 and a detector 14 capable of detecting the X-rays emitted by the tube 13. This arm 12 may be oriented vertically, horizontally or obliquely. The tube 13 is provided with a focus 15 which is the X-ray emitting focus. This focus 15 emits an X-ray beam 16 along a main direction of emission D.

The arm 12 is hinged on the vertical column 11 in such a way that it can be used to shift the tube 13 along a path T in the form of a circle arc while, at the same time, leaving the detector 14 immobile. Other arrangements are possible, enabling the tube 13 to move in a plane or in a sphere portion. The tube 13 can then take up different positions spread in a tilt between two extreme positions. These two positions are, for example, symmetrical to each other relative to the perpendicular to the plane of the detector 2.

In a preferred example, the detector 14 is a digital detector. The detector 14 is hooked to the arm 11 opposite the tube 13 and in the main direction of irradiation D, so as to receive the X-ray beam 16.

The arm 12 is provided with a breast-support tray or platform 17 upon which a patient lays her breast. This breast-support tray is laid over the detector 14. The detector 14 is placed beneath the breast-support tray 17. The detector 14 detects the X-rays that have gone through the patient's breast and the breast-holder tray 17.

In one variant, the detector 14 may be mobile and may take up various positions around the breast at the same time as the X-ray tube 13. In this case, the detector 14 is no longer fixedly joined to the breast-holder tray 17. The detector 14 may be flat or curved. It may be shifted rotationally and/or in translation In a preferred example, the detector 14 is a digital detector. The detector 14 is hooked to the arm 12 opposite the tube 13 and in the direction of emission D, so as to receive the X-ray beam 16.

The arm 12 is provided with a breast-holder tray 18 on which a patient lays her breast. This breast-holder tray 18 is placed on top of the detector 14. The detector 14 is placed beneath the breast-holder tray 18. The detector 14 detects the X-rays that have crossed the patient's breast and the breast-holder tray 18.

Furthermore, for reasons related both to the immobilizing of the breast and to image quality or intensity of X-rays delivered to the patient's breast, it is necessary to compress the patient's breast during the radiography. Various compression forces may be applied. These forces are applied through a compression pad 18 which compresses the breast on the breast-holder tray 17 as a function of the type of examination to be made. To this end, the arm 12 has a sliding pad 18 that can be made to compress the breast either manually or in being motor-driven. The pad 18 is made out of an X-ray transparent material, for example plastic. The arm 12 therefore bears the following vertically: starting from the top, the X-ray tube 13, the compression pad 18, the breast-holder tray 17 and the detector 14.

While the pad 18, the patient's breast, the tray 17 and the detector 14 are fixed, the X-ray tube 13 may take up various positions in space relative to this assembly.

To enable the study of each part of the patient's breast, the beam 16 may be oriented in a multitude of directions about said breast. After having received the multitude of beams 16 which cross a part of the patient's body, the detector 14 emits electrical signals corresponding to the energy of the rays received. These electrical signals may then be transmitted to a control logic unit 20 by means of an external bus 21. These electrical signals enable this control logic unit 20 to produce a projection image corresponding to the part of the body analyzed. These images can then be displayed by means of a screen of this control logic unit 20 or they may be printed.

In one example, the control logic unit 20 comprises a microprocessor 22, a program memory 23, a data memory 24, a display screen 25 provided with a keyboard 26 and an output/input interface 27. The microprocessor 22, the program memory 23, the data memory 24, the display screen 25 provided with a keyboard 26 and the input/output interface 27 are interconnected by an internal bus 28.

In practice, when a device is said to have performed an action, this action is performed by a microprocessor of the device controlled by instruction codes recorded in a program memory of the device. The control logic unit 20 is such a device. The control logic unit 20 is often made in integrated-circuit form.

The program memory 23 is divided into several zones, each zone corresponding to instruction codes in order to fulfill one function of the device. Depending on the variants of the invention, the memory 23 has a zone 29 comprising instruction codes to set up a path of the tube 13. The memory 23 has a zone 30 comprising instruction codes to determine the number of angles of orientations of the direction D along the path. The memory 23 has a zone 31 comprising instruction codes to determine the mode of spreading out the orientations of the direction D according to the class of the radiology signs to be detected. The memory 23 has a zone 32 comprising instruction codes to implement a strategy of distribution of X-ray intensities on the multiplicity of orientations of the main direction D of X-ray irradiation depending on the class and size of the radiology signs to be detected.

The memory 23 has a zone 33 comprising instruction codes to command the emission of the X-ray intensities assigned to each orientation of the main direction D of X-ray irradiation.

The memory 23 has a zone 34 comprising instruction codes to acquire the projection images received by the detector 14 corresponding to the X-rays emitted at each orientation. The memory 23 has a zone 35 comprising instruction codes to carry out a pre-processing of the projection images in order to eliminate artifacts due to the acquisition geometry and the detector. The memory 23 has a zone 36 comprising instruction codes for the application, to each projection image, of a filter that is adaptive as a function of the X-ray intensity received per corresponding direction D.

The memory 23 has a zone 37 comprising instruction codes to apply a tomography reconstruction algorithm to all the processed projection images acquired at different angles in order to obtain a reconstructed digital volume comprising 50 to 80 slices for an average breast. The memory 23 has a zone 38 comprising instruction codes to execute an algorithm for the processing of the reconstructed digital volume in order to localize voxels capable of constituting radiology signs, in the volume of the reconstructed breast. These radiology signs may be microcalcifications or opacities.

In operating mode, the control logic unit 20 determines a path T of the tube 13. This path may be determined according to a standard view chosen by the practitioner.

The control logic unit 10 proceeds by sampling a series of exposure positions of the tube 3 along the path T. The shape of the path T is given by the of the focus 15. In the example of FIG. 3, the path T has the shape of a circle arc. These exposure positions of the tube are demarcated by two borderline exposure positions of the tube. These borderline exposure positions are generally produced by virtue of the construction of the tube or else according to medical requirements. These borderline exposure positions correspond to the extreme positions that the focus can occupy in space. The two borderline exposure positions are symmetrical relative to a middle position perpendicular to the plane N of the breast-holder tray 17. The breast and hence the detector 14 are thus irradiated during consecutive exposure positions. For these exposure positions, the focus 15 of the X-ray tube occupies fixed, angularly spread-out positions in space.

In one example, and although this cannot be considered to be limit the invention, it is planned that the angular exploration will be equal to 60 degrees plus or minus 30 degrees relative to a median direction of irradiation which is the middle exposure position. During this exploration, the control logic unit acquires a certain number of beams 16, for example 9, 11, 13 or another number of beams, depending on the desired precision of image reconstruction. Thus, during an exposure of the patient's breast, the tube 13 subjects the breast to X-ray irradiation. In one example, the tube 13 subjects the breast to a first X-ray irradiation whose main direction D of irradiation is oriented in a first middle angle of orientation A0 perpendicular to the plane N of the breast-holder tray. This exposure is the time during which the breast is exposed to X-rays. This exposure of the breast is considered to be fixed when the tube 13 subjects the breast to irradiation in fixed positions. And the exposure of the breast is considered to be mobile when the tube 13 subjects the breast to irradiation in non-fixed positions.

This middle orientation angle A0 is perpendicular to the normal of the detector when the detector is fixed. The middle orientation angle A0 corresponds to the angle of the main direction when the tube is in the middle exposure position. The control logic unit 20 determines the number of orientations of the main direction D of X-ray irradiation along the path T of the tube 13. In the example of FIG. 3, the number of orientations is 21.

The tube 13 emits X-ray doses for the multiplicity of orientations of the main direction of irradiation D along the path T. In the example of FIG. 3, only the orientations situated between the middle orientation A0 and the borderline orientation A9 are represented. Here the orientation A9 angle corresponds to the angle of the main direction when the tube is in a borderline exposure position.

These orientations A1 to A9 are situated to the right of the middle orientation A0. The other orientations A'1 to A'9, not shown, are situated to the left of the middle orientation A0. These orientations A'1 to A'9 have the same characteristics as the orientations A1 to A9. The middle orientation A0 separates the total number of orientations into two equal parts.

Figure 5A:
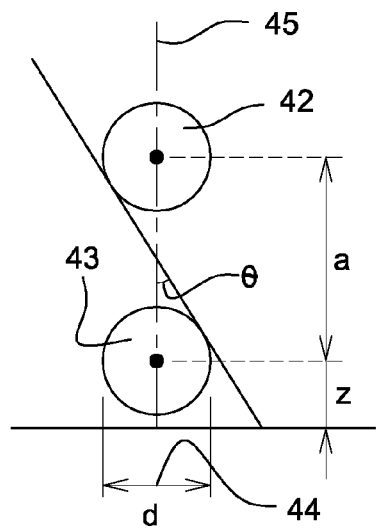
FIGS. 5a to 5c show a mode for determining an angular distribution of exposure positions of the tube as well as a strategy of distribution of the X-ray intensities according to the invention.
Figure 5B:
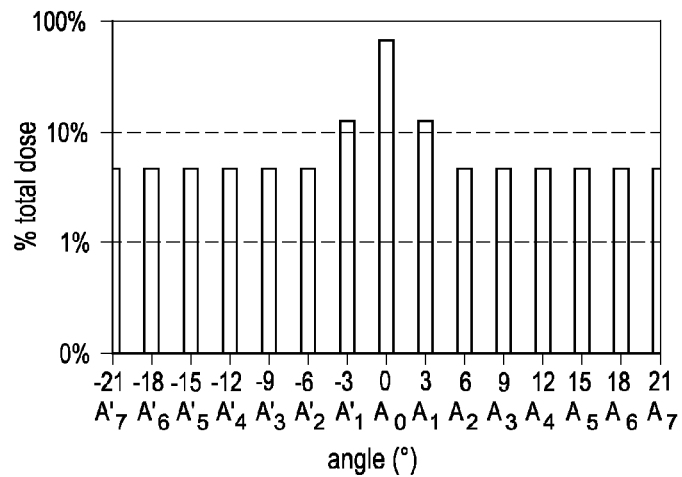
Figure 5C:
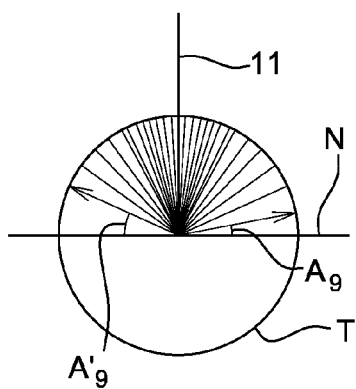

The control logic unit also determines the angular spread-out of the orientations A0 to A9 to emit the multiplicity of beams 16 along the path T. The control logic unit 20 spreads out the orientations 16, A0 to A9, on the path T as a function of the class of the radiology sign to be detected. One example of the determining and angular spread-out of the orientations is shown in FIGS. 5a and 5c.

The control logic unit 20 determines the X-ray intensities, more commonly known as doses, to be distributed on the X-ray beams 16 of each orientation of the direction D. The total X-ray doses to be distributed may be determined as a function of the dose used in conventional mammography. In one variant it may be determined as a function of the thickness of the patient's breast.

The control logic unit 20 determines the mode of distribution of the total dose among the orientations of the direction D. It determines a favored orientation or a favored group of orientations whose received accumulated dose is the highest assigned X-ray dose. An example of this determining operation is shown in FIGS. 4b and 5b. The control logic unit 20 distributes the X-ray intensities non-uniformly on the beams 16 of the directions D. The control logic unit causes the irradiation dose produced by the X-ray tube to vary during the exposure as a function of the orientation A0 to A9 of the main direction relative to the body. An exemplary embodiment of such a distribution is shown in FIG. 5b.

The detector 14 acquires a multiplicity of projection images representing the multiplicity of main directions of irradiation D. The control logic unit applies an adaptive filter to each projection image as a function of the intensity of X-rays received per corresponding direction D.

The control logic unit 20 acquires this multiplicity of filtered projection images in the data memory 24. By then applying image reconstruction algorithms of the type used in computerized tomography, it is possible to reconstruct the image in a slice plane as well as other images in planes adjacent to the slice plane. It is thus possible to speak of synthesis tomography in which all the images are acquired in a single scan. In practice, the image in the slice plane is more precise than the images in the adjacent planes when the exploration is not done on 180°.

The corrections implied by the synthesis relate as much to the fact that the path of the focus of the X-ray tube is not homothetic with the position of the detector as to the fact that the detector, along the different angles of incidence, shows a tilt relative to the normal direction of projection. The control logic unit corrects the effects of these acquisition constraints of computerized tomography reconstruction algorithms.

In order to obtain a full representation of the breast relative to the selected view, the control logic unit performs the same operations for the orientations A'1 to A'9 of the path T.

Figure 4A:
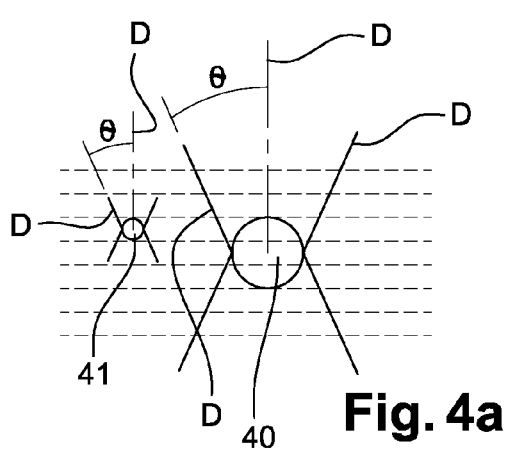
FIG. 4a is a schematic view of the effects of a strategy of distribution of doses in the prior art.
Figure 4B:
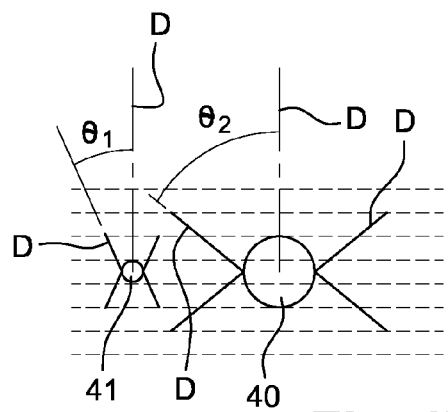
FIG. 4b is a schematic view of the effects of a strategy of distribution of doses in the invention.

FIG. 4a schematically represents a prior art strategy of uniform dose distribution. In the example of FIG. 4a, the orientations of the direction D have a uniform angular distribution θ. Similarly, the dose is distributed uniformly on the multiplicity of directions D. For each orientation, the detector gives a Z response along the projection axis which depends on the radius of projection of the breast.

With the mode of spread-out and distribution of FIG. 4a, the large-sized radiological signs of the breast such as the opacities 40 are detected with a high rate of selectivity. However, for small-sized radiological signs of the breast such as microcalcifications 41, the response will be very short, affecting the detectability of the lesion, independently of the reconstruction or display method used. This problem is due to the fact that, with the classic, uniformly distributed dose, the dose assigned to the orientations close to borderline orientations is excessive for the information delivered: this information is of little clinical use and may even have an adverse effect on the detection of lesions.

The invention resolves this problem by implementing a strategy of non-uniform distribution of the dose, as can be seen in FIG. 4b. In the example of FIG. 4b, this dose distribution strategy enables an anisotropic 3D reconstruction of the breast. Thus, the Z responses of the radiology signs detected are defined as a function of a clinical goal which is a simultaneous detection of large-sized and small-sized radiology signs with optimum use of the dose. With this type of strategy, the effective angle of orientation changes with the size of the radiology sign to be detected.

FIG. 5a shows a mode of determining the angular spread-out along the path of the tube. In tomosynthesis, the angular spread-out has an important effect on the superimposition of the tissues. Consequently, to determine the spread-out of the orientations between the borderline orientations, the control logic unit considers two identical, homogeneous spherical structures 42 and 43 with a coefficient of attenuation $\mu$ and a diameter 44 of a length d. These two spherical structures 42 and 43 have a distance a between their centers along the same vertical axis 45. The angle $\theta$ needed to discriminate the spherical spheres 42 and 43 distinctly along the axis is defined by the minimum angle such that their projections are tangential.

On this basis, the control logic unit can compute the angle of spread-out of the orientations used to discriminate all the radiology signs present in the breast. In one example, the control logic unit may consider only two classes of radiology signs, namely the opacities and the microcalcifications. Other lesions may also be considered.

The opacities have a relatively low attenuation coefficient $\Delta\mu$ and a large diameter in the 2 mm<d<8 mm range and the microcalcifications have a higher attenuation coefficient $\Delta\mu$ and a smaller diameter d<1 mm. For each class of radiology signs, the control logic unit assigns a fixed separation distance a. The control logic unit computes the angle of spread-out of each orientation in effecting a variation in the diameter of the radiology signs with a constant separation pitch. In a preferred example, the control logic unit obtains a variation in the diameter of the microcalcifications with a constant separation pitch of 0.1 mm and the diameter of the opacities with a constant separation pitch of 1 mm.

This means that the angular ratio is considered to be relatively small for an angular spacing close to the middle orientation at 0 degrees and considered to be greater for the orientations close to the borderline orientations of the tube.

FIG. 5b gives a view in a preferred embodiment of a mode of distribution of the dose. In this example, the y-axis is formed by the percentage of X-ray intensities or dose and the x-axis is formed by the angles made respectively by each of the orientations of the main direction of irradiation with the middle orientation. The dose is distributed non-uniformly on the totality of the orientations A'9 to A9. The orientations are spread out angularly between two borderline orientations A9 and A'9 in groups of orientations. The groups of orientations are situated on either side of the middle orientation A0.

The control logic unit determines a favored orientation or a favored group of orientations for the path T. It assigns more than ⅝th of the total dose to this favored orientation or this favored group of orientations.

In the example of FIG. 5b, the middle orientation A0 is considered to be the favored orientation. The control logic unit assigns more than ⅝th of the total dose to the middle orientation A0. It is the one that receives the biggest dose. It receives 70% to 80% of the total dose. The orientations A'1 and A1 close to the middle orientation A0 receive 10% to 20% of the total dose. The orientations A'2 and A2 close to the middle orientation A0 receive 5% to 10% of the total dose.

The orientations A6, A7 and A'6, A'7 close respectively to the borderline orientations A9 and A'9 receive 1% to 3% of the total dose. The intermediate orientations A3, A4 and A'3, A'4 receive 3% to 5% of the dose. In this example, the control logic unit increases the dose when the orientation approaches the middle orientation A0.

The favored orientation is preferably the orientation whose main direction is perpendicular to the plane of the breast support. It may also be the orientation separating the total number of orientations into two parts. It can be defined according to the embodiments of the invention.

The control logic unit can also assign more than ⅝th of the total dose to a favored group of orientations. The orientations of this group of orientations are situated on either side of the favored orientation.

With the invention, it can thus be shown that a dose distribution with compensation to within the nearest angle of the optical axis of reconstruction, i.e., the axis perpendicular to the slice planes, improves the image quality. Consequently, any strategy whatsoever that corrects the distribution of the dose relative to that of the prior art offers better results for the detection of two classes of radiology signs such as microcalcifications or opacities.

In a preferred example, the strategy of distribution of the dose may be defined as follows. For a borderline group whose orientations are closest to a borderline orientation, the control logic unit gives an accumulated irradiation dose which is lower than one-ninth of the total irradiation dose. For a middle group, whose orientations are spread out on either side of the middle orientation, the control logic unit gives an accumulated irradiation dose that is greater than ⅝th of the total irradiation dose. And for an intermediate group placed between the middle group and the borderline group, the number of orientations of the group is smaller than the number of orientations of a borderline group.

With this type of distribution, the response along the projection axis is determined by the projected size of the breast and by the angular aperture of the acquisition. The dose is adjusted at each projection so that the information content does not allow for a decision on smaller radiological signs at the orientations belonging to the borderline groups. The content of the information given by the orientations of the middle group enables a decision on smaller radiology signs. This enables a reduction in the response of the large-sized radiology signs as compared with the response of the small-sized radiology signs. Consequently, by distributing the dose along an accurately designed angular profile, the response is made approximately and independently of the size of the breast. Thus, with the invention, a diameter and a class of radiology signs to be detected are assigned to each angle.

FIG. 5c is an example of a dose distribution profile. In the example of FIG. 5c, the control logic unit determines the distance of separation a for each class of radiology sign. For the class of microcalcifications, the distance a is defined as being equal to 2 mm. For the class of capacities the distance a is defined as being equal to 10 mm. The result of the computation of the angular spread-out of the orientations between two borderline orientations is shown in the table below.

The table has a first column providing information on the class of the radiology signs and on the value of the separation distance a. The second column of the table provides information on the diameters of the radiology signs to be detected. In this second column, the constant separation pitch is equal to 0.1 mm for the microcalcifications and 1 mm for the opacities. The third column gives the computation of the angles of spread-out of the orientations relative to the normal of the breast-support tray as a function of the diameter and class of the radiology signs to be detected. The fourth column gives computations of the angular pitch of the orientations. The angular pitch is the angle formed by two consecutive orientations.

|  | diameter (mm) | angles (°) | Angular pitch |
|---|---|---|---|
| Opacities |  |  |  |
| A = 10 mm | 10 | 90.00 |  |
|  | 9 | 64.16 | 11.03 |
|  | 8 | 53.13 | 8.70 |
|  | 7 | 44.43 | 7.56 |
|  | 6 | 36.87 | 6.87 |
|  | 5 | 30.00 | 6.42 |
|  | 4 | 23.58 | 6.12 |
|  | 3 | 17.46 | 5.92 |
|  | 2 | 11.54 |  |
| microcalcifications |  |  |  |
| a = 2 mm | 1 | 30.00 | 3.26 |
|  | 0.9 | 26.74 | 3.16 |
|  | 0.8 | 23.58 | 3.09 |
|  | 0.7 | 20.49 | 3.03 |
|  | 0.6 | 17.46 | 2.98 |
|  | 0.5 | 14.48 | 2.94 |
|  | 0.4 | 11.54 | 2.91 |
|  | 0.3 | 8.63 | 2.89 |
|  | 0.2 | 5.74 | 2.87 |
|  | 0.1 | 2.87 | 2.87 |

The combination of the results for the microcalcifications and the opacities gives an angular pitch $\theta \approx 3°$ for the orientations close to the middle orientation and an angular pitch $\theta \approx 7°$ for the orientations close to the borderline orientation.

The control logic unit determines the dose distribution strategy by computing the contrast that characterizes each radiology sign size of the table. To do this, the control logic unit assigns an attenuation coefficient $\Delta\mu=0.027$ mm$^{-1}$ to the opacities and a coefficient $\Delta\mu=0.714$ mm$^1$ to the microcalcifications. For each radiology sign size of the table, the control logic unit computes the corresponding attenuation coefficient. From this table of attenuation coefficients, the control logic unit determines a corresponding table of contrast of each size of radiology sign of the table. Then, the control logic unit uses a mathematical decision criterion, for example the Rose criterion, to compute the necessary dose by which it is possible to discriminate the radiology signs in the projection image as a function of the contrast computed for these radiology signs. Thus, by using the mathematical Rose criterion and on the basis of the contrast, the control logic unit determines the dose distribution strategy of FIG. 5b. Other types of mathematical criteria can be used to determine a dose distribution strategy.

The control logic unit 10 carries out an angular distribution of the orientations between the borderline orientations of the path T according to the results of the table. The control logic unit assigns each orientation the computed X-ray dose. This non-uniform distribution of the dose can be used to obtain high contrast of the cancer cells. This dose is preferably equal to the dose used in the prior art to obtain two radiography projections in standard mammography.

In a preferred embodiment, the control logic unit 10 assigns a greater dose to the orientations close to the middle orientation.

The control logic unit 10 can first of all command X-ray emission in the middle orientation before emitting in the other orientations. It can also command emission in the orientations close to the borderline orientations before emitting in the orientations close to the middle orientation. It can also command emission only in the orientations situated to the right of the middle orientation. In this case, it determines the orientations situated to the left of the middle orientation, considering the middle orientation to be the bisector of the two parts.

The detector 14 acquires the projection images representing the emissions in the orientations of the path T. The processing of the projection images is shown in FIG. 6.

Figure 6:
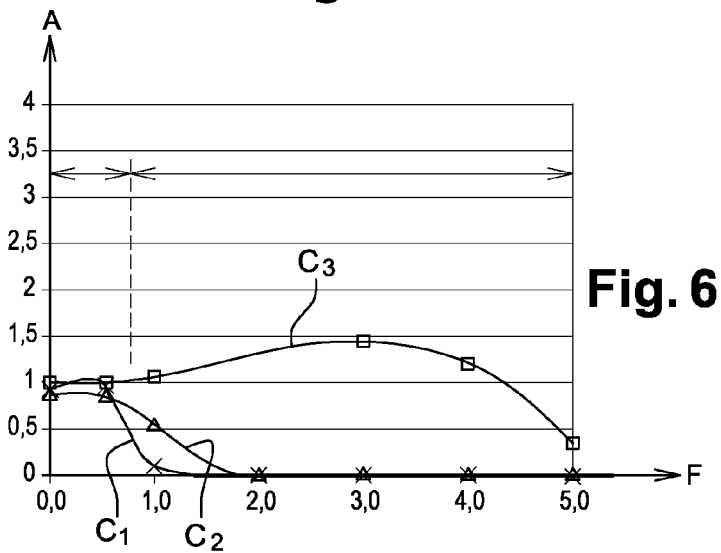
FIG. 6 is a graphic view of adaptive filters to be applied to each projection image according to the invention.

FIG. 6 is a graphic representation of an adaptive filter to be applied to each projection image. The y-axis represents the amplitude in mm. The x-axis represents the spatial frequency. The projection images are processed by an adaptive spatial filter required to control the propagation of the noise during the reconstruction step.

The spatial filter has a filtering core of a given size. The size of the core is smaller for the projection images corresponding to the orientations close to the middle orientation then it is for the projection images corresponding to the orientations close to the borderline orientations.

In a preferred example, these spatial filters are Wiener filters. A particular implementation of the filters is described in the document FR28 64 299 A. The control logic unit applies a Wiener filter to each piece of image data as a function of the X-ray dose assigned to this projection image.

FIG. 6 shows three curves C1 to C3 of Wiener filters corresponding to two dose levels and three types of radiology signs. The curve C1 represents a Wiener filter applied to a projection image whose assigned dose is at a 0.1% to 5% of the total dose and whose radiology sign to be detected has a diameter of 3.6 mm. This projection image is given at an orientation close to the borderline orientation. The radiology sign here is an opacity.

The curve C2 represents a Wiener filter applied to a projection image for which the assigned dose is at 0.06% to 5% of the total dose and whose radiology sign to be detected has a diameter of 2 mm. This projection image is given to an orientation that is an intermediate orientation between the middle orientation and the borderline orientation. The radiology sign here is an opacity.

The curve C3 represents a Wiener filter applied to a projection image for which the assigned dose is at 0.3% to 30% of the total dose and whose radiology sign to be detected has a diameter of 0.5 mm. This projection image is given to an orientation close to the middle orientation. The radiology sign here is a microcalcification.

As can be seen in FIG. 6, the assigned dose and the size of the core vary gradually and monotonically with the identification of the angle of orientation relative to the middle orientation. The values of the filters are generally decreasing as a function of the spatial frequency. The values of the filters for the orientations close to the middle orientation are greater than the values of the filters for the orientations close to the borderline orientation.

This, each orientation has an assigned size and the radiology sign class, a dose, and a curve related to the spatial frequency. For each orientation, the control logic unit determines a Wiener filter from the curve linked to the spatial frequency and the modulation transfer function, in assuming that the input signal is the radiology signal to be detected with a diameter and a given contrast associated with this orientation.

The filters have the function of preserving the signal-to-noise ratio for the small-sized radiology signs such as the microcalcifications during the reconstruction step. This preservation is done by eliminating the high-frequency contribution of these low-dose projections to the noise spectrum during the reconstruction.

This angular spread-out of the orientations reduces the superimposition of the tissues. The method of distribution of the dose gives a better use of the total dose and as well as lower risk of missing structures with clinical interest.

Figure 7:
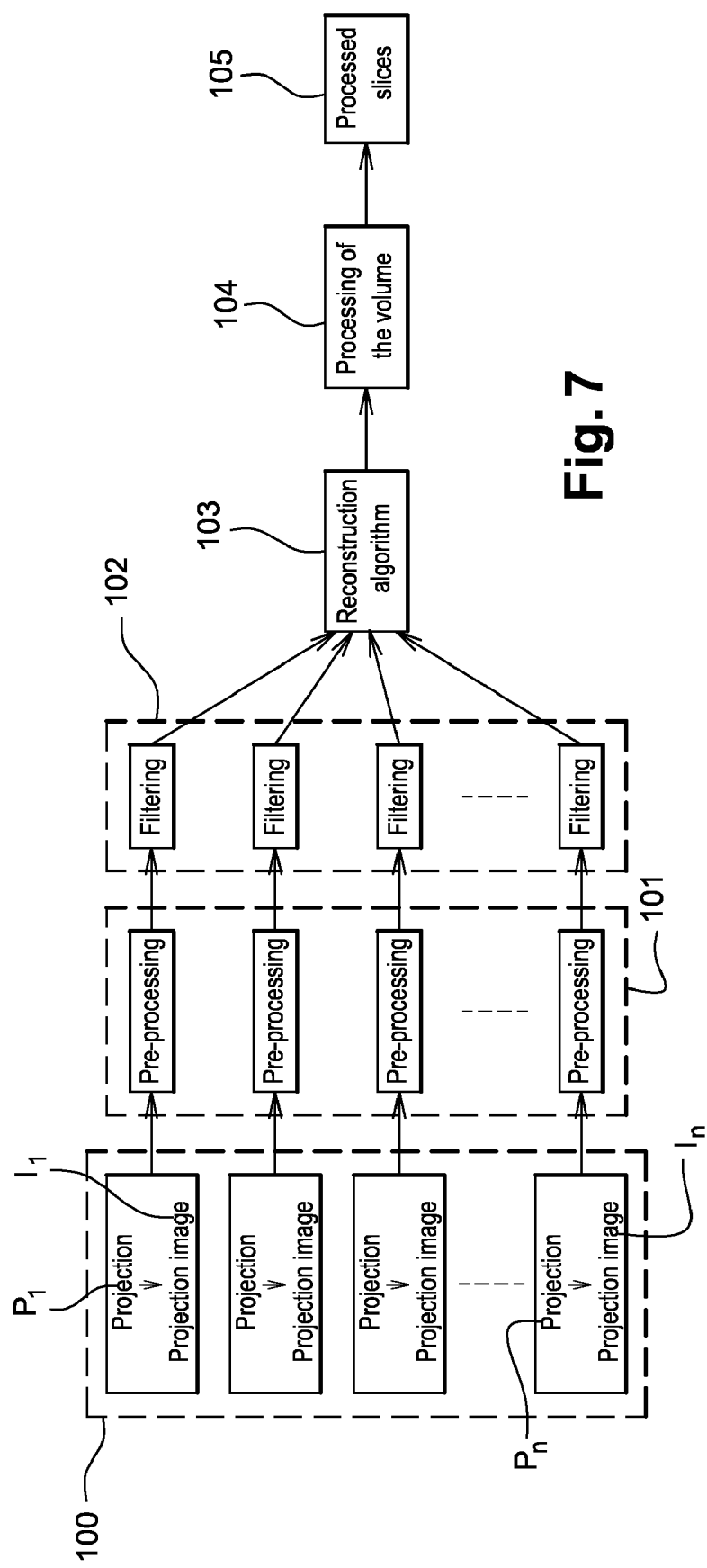
FIG. 7 illustrates means implementing the method of the invention.

FIG. 7 illustrates means implementing the method of the invention. In FIG. 7, at the step 100, the X-ray tube 3 emits X-ray intensities going through the patient's breast for a multiplicity of projections P1 to Pn, according to a pre-determined path T. These X-ray intensities are distributed among the projections according to a strategy described in FIGS. 5a to 5c.

The detector 4 acquires the X-ray projection images I1 to In representing respectively the projections P1 to Pn. The control logic unit processes the projection images I1 to In.

At the step 101, the control logic unit applies the pre-processing algorithm to each projection image I1 to In.

At the step 102, the control logic unit applies the Wiener filter as described in FIG. 6 to each pre-processed projection image. At the step 103, the control logic unit applies a simple back-projection reconstruction algorithm. This algorithm is used to reconstruct the volume in different slice planes parallel to the detector. The term used here is tomosynthesis of the breast. All the pre-processed and filtered images I1 to In are used during this tomosynthesis reconstruction to provide a digital volume of the breast. This tomosynthesis technique enables the reconstruction of the 3D volume of the breast being studied from a small number of 2D projections or projection images, distributed over a limited angular domain and acquired on a digital detector.

At the step 104, the control logic unit applies a processing algorithm to the digital volume. This processing algorithm can be any type of prior art algorithm used to process and detect radiology signs in a digital volume. The method of the invention enables the processing algorithm to be more selective in the detection of radiology signs.

At the step 105, the control logic unit displays the processed slices of the reconstructed volume.

What is claimed is:

1. A method for obtaining a tomosynthesis image for a more selective detection of radiology signs, comprising:
   providing an X-ray irradiation dose by means of an X-ray tube for which a direction of the X-ray irradiation dose is oriented at an angle of orientation relative to a body;
   distributing the orientation of the direction along a path by changing the angle of orientation between two borderline orientations;
   exposing the body to the X-ray irradiation at each of the orientations; and
   varying the X-ray irradiation dose produced by the X-ray tube during the exposure as a function of the orientation of the direction relative to the body,
   wherein the angle of orientation changes with the size of radiology sign,
   wherein one orientation or one group of orientations is favored relative to the multiplicity of orientations of the path, and
   wherein the accumulated irradiation dose of the favored orientation or of the favored group of orientations is greater than ⅝th of the total irradiation dose.

2. A method according to claim 1, wherein the orientations are situated on either side of a middle orientation whose main direction is perpendicular to a support of the body;

wherein for a borderline group of orientations closest to the borderline orientations the accumulated irradiation dose is smaller than 1/5th of the total irradiation dose;

wherein for a middle group of orientations distributed on either side of the middle orientation the accumulated irradiation dose is greater than 3/5th of the total irradiation dose; and wherein for an intermediate group of orientations between the middle group of orientations and a borderline group of orientations the number of orientations in the intermediate group is smaller than the number of orientations of the borderline group, and the accumulated irradiation dose is equal to the remaining fraction of the total irradiation dose.

3. A method according to claim 1, wherein the angle formed by two consecutive orientations increases towards the borderline orientation.

4. A method according to claim 1, wherein the body is a breast.

5. A method according to claim 4, further comprising:
determining the X-ray irradiation dose produced by the X-ray tube as a function of the thickness of the breast.

6. A method according to claim 1, further comprising cutting the reconstructed image into one or more slices relative to a slicing plane parallel to the detector.

7. A method for obtaining a tomosynthesis image, comprising:
providing an X-ray irradiation dose by means of an X-ray tube for which a direction of the X-ray irradiation dose is oriented in an angle of orientation relative to the body;
recording a first projection image corresponding to the first orientation;
distributing the direction of orientation angularly between two borderline orientations situated on either side of a middle orientation, and recording other projection images; and
processing the projection images to produce a reconstructed image, wherein the angle of orientation changes with the size of radiology sign, wherein the X-ray irradiation dose for the exposure oriented close to the borderline orientations is smaller than the X-ray irradiation dose for the X-ray exposure oriented close to the middle orientation, wherein the processing applying a spatial filter to each of the projection images, wherein the spatial filter comprises a filtering core the size of which is smaller for the projection images corresponding to the orientations close to a middle orientation than it is for the projection images corresponding to the orientations close to the borderline orientations.

8. A method according to claim 7, further comprising varying the X-ray illumination dose and the size of the filtering core gradually and monotonically with the identification of the angle of orientation relative to the middle orientation.

9. A method according to claim 7, wherein the spatial filter comprises Wiener filters and the spatial filter for the orientations close to the middle orientation is different than the spatial filter for the orientations close to the borderline orientation.

10. A method according to claim 7, wherein the angle between orientations close to the middle orientation is equal to about 3 degrees, and the angle between orientations close to the borderline orientation is equal to about 7 degrees.

11. A method according to claim 7, wherein the middle orientation is oriented perpendicularly to a support of the body, and wherein the support faces the X-ray tube.

* * * * *

UNITED STATES PATENT AND TRADEMARK OFFICE
CERTIFICATE OF CORRECTION

| | | |
|---|---|---|
| PATENT NO. | : 7,697,661 B2 | Page 1 of 1 |
| APPLICATION NO. | : 11/830902 | |
| DATED | : April 13, 2010 | |
| INVENTOR(S) | : Souchay et al. | |

It is certified that error appears in the above-identified patent and that said Letters Patent is hereby corrected as shown below:

In Column 16, Line 3, in Claim 7, delete "of" and insert -- of the --, therefor.

In Column 16, Line 10, in Claim 7, after "processing" insert -- comprises --, therefor.

Signed and Sealed this
Thirteenth Day of September, 2011

David J. Kappos
*Director of the United States Patent and Trademark Office*